United States Patent
Raybin et al.

(10) Patent No.: US 9,539,055 B2
(45) Date of Patent: Jan. 10, 2017

(54) RESECTION DEVICE WITH SUPPORT MECHANISM AND RELATED METHODS OF USE

(71) Applicant: Boston Scientific Scimed, Inc., Maple Grove, MN (US)

(72) Inventors: Samuel Raybin, Marlborough, MA (US); Paul Smith, Smithfield, RI (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 268 days.

(21) Appl. No.: 14/185,690

(22) Filed: Feb. 20, 2014

(65) Prior Publication Data

US 2014/0276908 A1 Sep. 18, 2014

Related U.S. Application Data

(60) Provisional application No. 61/780,362, filed on Mar. 13, 2013.

(51) Int. Cl.
| | | |
|---|---|---|
| *A61B 17/24* | (2006.01) | |
| *A61B 18/14* | (2006.01) | |
| *A61B 17/3205* | (2006.01) | |
| *A61B 18/00* | (2006.01) | |

(52) U.S. Cl.
CPC ....... *A61B 18/149* (2013.01); *A61B 17/32056* (2013.01); *A61B 18/1492* (2013.01); *A61B 2018/00601* (2013.01); *A61B 2018/141* (2013.01); *A61B 2018/1475* (2013.01)

(58) Field of Classification Search
CPC ............ A61B 17/221; A61B 17/32056; A61B 18/1492; A61B 2017/2212; A61B 17/24; A61B 18/149

See application file for complete search history.

(56) References Cited

U.S. PATENT DOCUMENTS

| | | | | |
|---|---|---|---|---|
| 5,078,716 A | * | 1/1992 | Doll | A61B 18/14 606/47 |
| 5,437,665 A | * | 8/1995 | Munro | A61B 18/14 606/41 |
| 2013/0018384 A1 | | 1/2013 | Kappel et al. | |

FOREIGN PATENT DOCUMENTS

WO WO 2013/119970 A1 8/2013

OTHER PUBLICATIONS

International Search Report and Written Opinion for corresponding International Application No. PCT/US2014/017466, mailed Oct. 10, 2014, 11 pages.

* cited by examiner

*Primary Examiner* — Victor Nguyen
(74) *Attorney, Agent, or Firm* — Bookoff McAndrews, PLLC

(57) ABSTRACT

A medical device for resecting tissue. The medical device includes a catheter shaft having a proximal portion and two or more distal branch portions. The distal branch portions are moveable between a closed position, and an open position. One or more lumens extend between the proximal portion and through each distal branch portion. An actuation element extends through the lumen of each distal branch portion. A snare loop is connected to each actuation element.

16 Claims, 3 Drawing Sheets

RESECTION DEVICE WITH SUPPORT MECHANISM AND RELATED METHODS OF USE

CROSS-REFERENCE TO RELATED APPLICATIONS

This application claims the benefit of priority from U.S. Provisional Application No. 61/780,362, filed on Mar. 13, 2013, the entirety of which is incorporated by reference herein.

FIELD

Embodiments of the present disclosure relate generally to medical devices and procedures. In particular, embodiments of the present disclosure relate to medical devices to perform tissue resection and/or retrieval during minimally invasive medical procedures.

BACKGROUND

Tissue resection procedures, such as colonoscopy and polypectomy, are carried out by inserting introduction sheaths, such as endoscopes or laparoscopes, into the body of a patient through incisions or natural anatomical openings (e.g., oral, vaginal, and/or anal cavities). Commonly, such devices employ snares, typically designed as loops, for performing tissue resection procedures. However, snares have a tendency to slip off targeted tissue, often requiring repeated efforts to capture the tissue before the resection procedures can be successfully performed. In addition, a typical snare has low stiffness and requires a shallow angle of approach. These properties may reduce operability of the snare during the resection procedure.

Various methods have been developed to improve the functioning of snares. For example, one common approach is to apply a downward force on the snare to improve traction between the snare and the unwanted tissue. This downward force is usually limited due to a lack of stiffness in the snare, which may cause the distal end of the snare to deflect away from the tissue. In order to control this deflection, the downward force may continue to be applied or it may be increased until the tissue is snared. Continued or increased applied force increases the risk of accidentally damaging surrounding tissues, as well as increases the time required to complete a procedure. Further, it may be sometimes difficult to apply the necessary downward forces due to geometric and physical limitations such as shallow angle of approach required by the snare.

Therefore, there exists a need in the art for an improved snare with better engagement capabilities, thereby allowing consistent capture, excision, and/or removal of unwanted tissue.

SUMMARY

Embodiments of the present disclosure provide a device for resecting an undesired mass from a patient's body using a minimally invasive surgical system.

In accordance with an aspect of the present disclosure, the resection device may include a catheter, including a proximal portion having a first lumen, a first distal branch portion having a second lumen, and a second distal branch portion having a third lumen. The first and second distal branch portions are movable between a first position, wherein the first and second distal branch portions are disposed relative to one another at a first angle, and a second position, wherein the first and second distal branch portions are positioned relative to one another at a second angle greater than the first angle. The catheter includes first and second actuation elements extending, respectively, through the second and third lumens; and a snare loop connected at a first location to the first actuation element and connected at a second location to the second actuation element.

In certain embodiments, the second and third lumens are connected with the first lumen. Portions of the snare loop are retracted within the second and third lumens when the first and second branch portions are in the first position. The first and the second actuation elements in the first and second distal branch portions are connected to a proximal actuation element in the first lumen. The first and the second actuation elements in the distal branch portions are connected to separate actuation elements in the proximal portion. The first and the second actuation elements affect movement of the first and second distal branch portions between the first and second positions. A sheath is disposed over the catheter portion. The sheath is configured to extend over the branch portions to affect movement of the branch portions between the first and second positions. The first and the second actuation elements and the snare loop are configured to conduct electricity. The first actuation element is attached to the snare loop at a first joint and the second actuation element is attached to the snare loop at a second joint. The first and second joints are located on opposite sides of the snare loop.

In accordance with another aspect of the present disclosure, a medical device includes an elongate member having a proximate end, a distal end, and a lumen formed therein, wherein the distal end splits into two or more branches, each branch having a lumen formed therein; and an expandable wire loop configured to transition between a collapsed configuration and an expanded configuration, and disposed at least partially within the two or more branches when in the collapsed configuration.

In certain embodiments, the lumens of the two or more branches are in connection with the lumen of the elongate member. The medical device includes a first actuation element slidably disposed within the lumen of the elongate member, a second actuation element slidably disposed within a lumen of one of the two or more branches, and a third actuation element slidably disposed within a lumen of another one of the two or more branches; wherein the second and third actuation elements are connected at respective proximal ends to the first actuation element and at respective distal ends to the expandable wire loop. Each of the two or more branches is configured to move between an open configuration and a closed configuration.

In accordance with another aspect of the present disclosure, a method for manipulating tissue, includes inserting a medical device within a body cavity. The medical device is a catheter, including a proximal portion having a first lumen, a first distal branch portion having a second lumen, and a second distal branch portion having a third lumen. The first and second distal branch portions are movable between a first position, wherein the first and second distal branch portions are disposed relative to one another at a first angle, and a second position, wherein the first and second distal branch portions are positioned relative to one another at a second angle greater than the first angle. The device also includes first and second actuation elements extending, respectively, through the second and third lumens; and a snare loop connected at a first location to the first actuation element and connected at a second location to the second actuation element. The method also includes: advancing an introduction sheath to a desired location within the body; extending the snare distally from the introduction sheath; deploying the snare over the tissue to be resected; and manipulating the tissue with the medical device.

In certain embodiments, the method also includes retracting the medical device from the body cavity. In certain embodiments, the method also includes deploying the snare loop distally from the second and third lumens in the first and the second distal branch portions respectively. The distal and proximal movements of the first and second actuation elements respectively move the snare loop into and out of the second and third lumens. The distal and proximal movements of the first and second actuation elements, respectively, expand and collapse the snare loop.

Additional objects and advantages of the claimed disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a user when introducing a device into a patient. The term, "proximal" refers to the end closest to the user when placing the device into the patient.

Overview

Embodiments of the present disclosure relate to medical devices used to retrieve and/or sever unwanted tissue as well as other unwanted material, such as stones, within a patient's body. For example, embodiments of the disclosed device may facilitate removal of unwanted tissue, such as, for example, cancerous polyps or lesions, from within a patient's body, including tissue disposed on, e.g., the mucosal walls of the colon, esophagus, stomach, or duodenum. A physician may also desire to resect tissue in order to conduct a procedure such as polypectomy or mucosectomy. It should be noted that devices presented in the present disclosure can be used both for retrieving and for severing target tissue or objects. For convenience, the medical devices discussed here will be referred to as resection devices; however, it should be understood that such devices are equally useful for retrieving unwanted tissue.

In some embodiments, a resection device may include a single or multi-lumen catheter shaft having at least one lumen that splits distally into two or more single-lumen branches. Each single-lumen branch may contain an actuation element, which may be made of a conductive material to serve as an electrical path for cautery cutting. Each actuation element may connect at respective distal ends, at a location along the circumference of a snare loop. The actuation elements may connect proximally to form a single actuation element within a single lumen.

Exemplary Embodiments

The embodiments disclosed herein may be used along with an endoscopic system, which may be used to introduce the disclosed embodiments to a target site within a patient's body. However, it may be noted that the embodiments of the present disclosure may also be used along with other introduction devices and systems, such as trocars, catheter sheaths, or the like.

Figure 1:
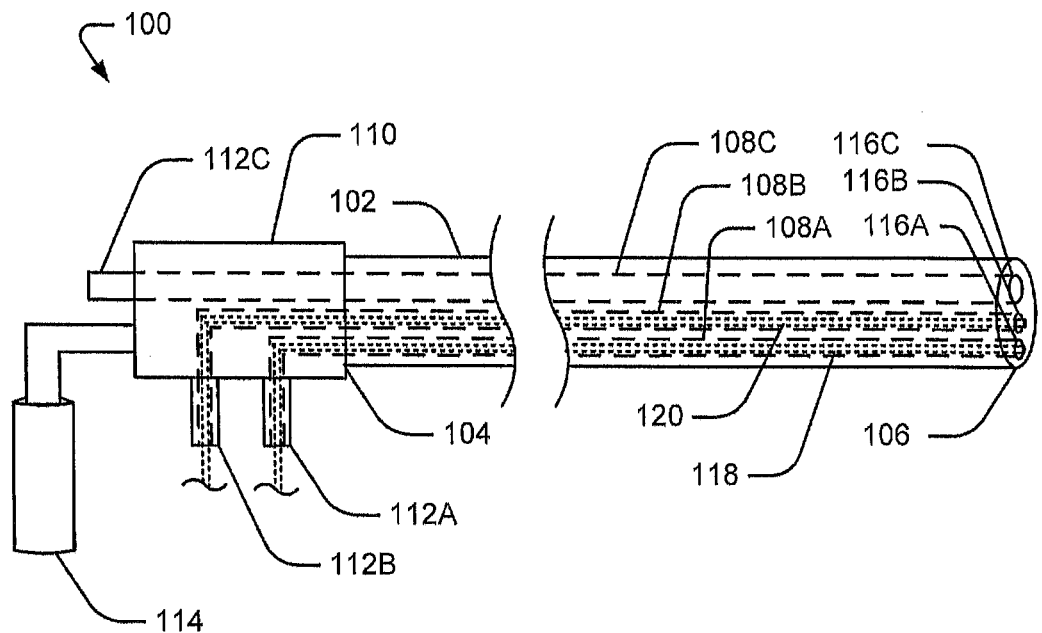
FIG. 1 illustrates an exemplary endoscopic system, according to an embodiment of the present disclosure.

FIG. 1 illustrates an exemplary endoscopic system 100. The system 100 may include an introduction sheath 102 having a proximal portion 104, a distal portion 106, and multiple working channels e.g., 108A, 108B, 108C extending therebetween. The system 100 further may include a hub assembly 110. Hub assembly 110 may be attached to the proximal portion 104 of introduction sheath 102, and may include a number of ports e.g., 112A, 112B, 112C, adapted to accommodate the introduction of a number of medical devices, as discussed in detail below. Mutually interacting attachment means (not shown), such as a Luer lock assembly, may be provided on the hub assembly 110 and introduction sheath 102, allowing those elements to be firmly joined. A handle 114 may also be provided, allowing a physician to control the operation of introduction sheath 102 and its accompanying devices. In some embodiments, handle 114 and hub assembly 110 may be combined into a single integral unit.

The introduction sheath 102 may be configured with appropriate length and cross-sectional dimensions to be navigated to a desired location within a patient's body. In addition, the introduction sheath 102 or a portion thereof may be steerable, which may allow the introduction sheath 102 to traverse circuitous paths within the patient's body. The channels 108A, 108B, 108C, may be configured to slidably accept one or more medical devices, communicate with the ports 112A, 112B, and 112C, and may have corresponding distal openings 116A, 116B, 116C, allowing respective medical devices to interact with the target tissue within the patient's body. An illumination device 118 and an optical device 120 may be fixedly or slidably disposed within channels 108A, 108B, respectively. For example, an illumination device 118, such as, a Xenon light source, LEDs, or the like, may provide illumination to visualize the target site with the help of optical device 120, such as a camera, a borescope, or the like. The handle 114 may facilitate an operator's manipulation of the system 100. Further, the handle 114 may include actuation elements (not shown) such as switches, knobs, gears or the like to control the movement of the introduction sheath 102 within the patient's body. The introduction sheath 102 may be introduced into a patient's body through an incision or a natural opening.

Figure 2:
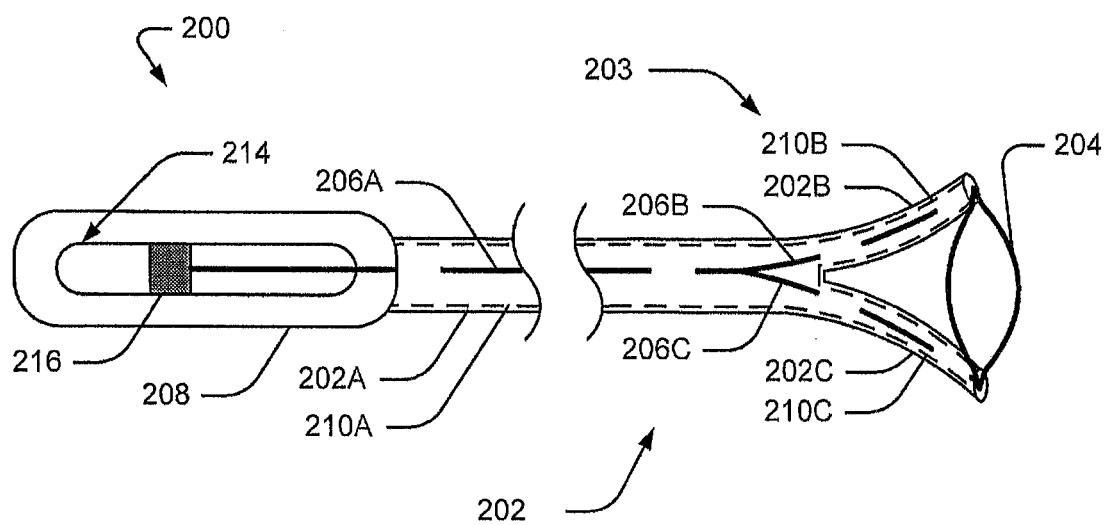
FIG. 2 depicts an exemplary resection device, for use with the exemplary endoscopic system of FIG. 1, according to an embodiment of the present disclosure.

FIG. 2 depicts an exemplary resection device 200, which may include a catheter shaft 202, having a branch assembly 203 at its distal end and handle 208 at its proximal end. Catheter shaft 202 may comprise a proximal portion 202A and two or more distal branch portions 202B and 202C. A snare loop assembly may include a snare loop 204 extending between the ends of distal branch portions 202B and 202C, as well as actuation elements 206B, 206C, which may attach to and extend from snare loop 204, through the interiors of distal branch portions 202B and 202C. Actuation elements 206B, 206C may meet and join a single actuation element 206A, at a location between distal branch portions 202B and 202C and proximal portion 202A of catheter shaft 202. Actuation element 206A may extend through to handle 208, which may be attached at the proximal end of the proximal portion 202A.

Resection device 200 may be carried within and deployed from a working channel of an introduction sheath 102, such as channel 108C, as shown in FIG. 1. In some embodiments, resection device 200 may be carried completely within the channel 108C.

The catheter shaft 202 may be a substantially Y-shaped sheath. The distal branch portions 202B and 202C may be tubular, extending from the distal end of proximal portion 202A. Each branch portion may define a lumen 210B, 210C, opening respectively to proximal portion lumen 210A. The distal branch portions 202B and 202C may have similar lengths and similar cross-sectional dimensions, while proximal portion 202A may be substantially longer. In general, the cross-sectional dimensions of the catheter shaft 202 may be adapted to slidably dispose the catheter shaft 202 within channel 108C, or the lumen of any other introduction device, such as a laparoscope, endoscope, trocar or the like, used along with the resection device 200. In an exemplary embodiment, if the channel 108C has a 5 F diameter, the cross-sectional dimensions of catheter shaft 202 may be less than 5 F.

Distal branch portions 202B and 202C may translate between an open position, in which the two portions form a first angle with the catheter axis, and a closed position, in which the two portions form a second angle with the catheter axis, the second angle being less than the first angle. The branch portions 202B and 202C may be made from a material having sufficient flexibility to permit the branch portions to translate from one position to the other. In some embodiments, the distal branch portions 202B, 202C may be pre-formed in the open position, or the radial stiffness of the snare loop 204 may force the distal branch portions 202B and 202C into the open position. In some embodiments, the distal branch portions 202B and 202C may be in the closed position to fit within the channel 108C and may expand to the open position when distally extending beyond channel 108C through distal opening 116C. In some other embodiments, one or more actuation mechanisms known in the art (not shown), may be employed to translate the distal branch portions 202B and 202C between the open and the closed positions.

The catheter shaft 202 may be flexible along its entire length or adapted for sufficient flexure to navigate through turns. The catheter shaft 202 may also be sufficiently rigid to provide the necessary force to urge the catheter shaft 202 forward. The catheter shaft 202 or a portion of its length, such as the tip, may be selectively steerable. As will be understood by those of skill in the art, actuation mechanisms (not shown), such as pull wires or other actuators, may be used to selectively steer the catheter shaft 202.

Snare loop 204 extends from distal branch portions 202B and 202C, to capture unwanted tissue, such as a polyp or bleb. A physician may actuate actuation element 206A to move in a distal direction, i.e., toward the distal end of the shaft 202. This movement may cause actuation elements 206B and 206C to also move toward the distal direction. As such, snare loop 204 may extend from branch portions 202B and 202C and expand. Once the snare loop 204 is in position relative to the tissue to be resected, the physician may operate actuation elements 206A, 206B, 206C, to move in the proximal direction, i.e., toward the proximal end of the shaft 202. This movement may cause actuation elements 206B and 206C to move in the proximal direction. As such, snare loop 204 may be withdrawn into branch portions 202B and 202C and close. A physician may use an actuation mechanism 214 on handle 208, to open and close snare loop 204. In some embodiments, snare loop 204 can be energized, severing tissue by electrocautery.

Snare loop 204 may be an expandable loop of wire or other flexible, elongated material, extending between distal branch portions 202B and 202C. Snare loop 204 may be configured to sever tissue, and in some embodiments, the severing action may be provided by electrocautery, while other embodiments may employ a direct cutting action. Embodiments employing electrocautery may involve the snare loop 204 and associated elements being electroconductive, as discussed in more detail below. Embodiments that sever tissue by cutting action may include a wire or other cutting elements, such as a knife edge or saw teeth. In some embodiments, the wire may be braided.

The snare loop 204 may be pre-formed in a circular, oval, polygonal, or other geometry, and it may be configured to alternate between open and closed positions. In the open position, the snare loop 204 may assume its pre-formed shape, while in the closed position, the snare loop 204 may assume a substantially linear configuration. The closed configuration may result from portions of snare loop 204 being withdrawn into distal branch portions 202B, 202C. Two points on snare loop 204 may be connected to actuation elements 206B and 206C, as described in detail below. The dimensions of the snare loop 204 may be adapted to the size of the tissue to be resected and the conditions governing the contemplated procedure, such as the size of the body cavity or the like. Further, the snare loop 204 may be configured to conduct electrical energy for electrocautery.

Figure 4:
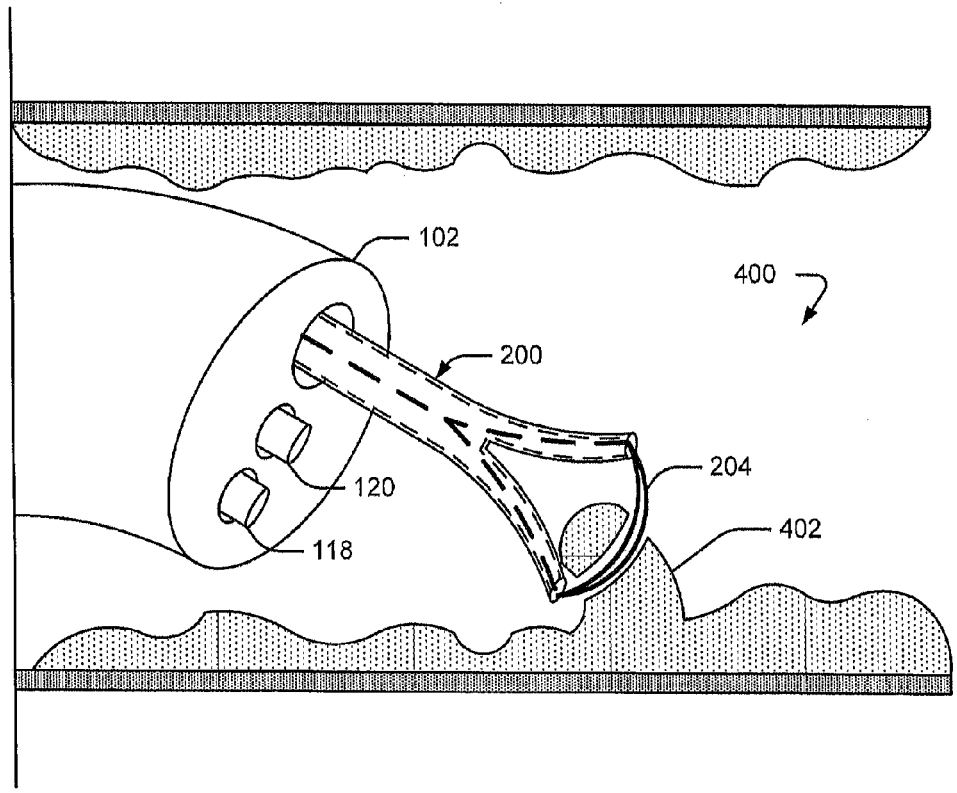
FIG. 4 exhibits an exemplary method of use of the resection device of FIG. 2.

The orientation of snare loop 204 in its open position can be chosen to suit a contemplated medical procedure. For purposes of illustration, FIG. 2 portrays snare loop 204 as lying in a plane passing through the longitudinal axis of the proximal portion 202A and the distal branch portions 202B, 202C. By altering the manner in which snare loop 204 is joined to actuation elements 206B, 206C, the plane defined by snare loop 204 may be angled with respect to the longitudinal axis of the proximal portion 202A. For example, FIG. 4 depicts a medical device 400 in which the plane described by snare loop 204 lies substantially perpendicular to the plane of proximal portion 202A and the distal branch portions 202B, 202C. The capability of tilting the snare loop 204 plane allows the designer to approach unwanted tissue in a desired direction for resection.

Actuation elements 206B, 206C may be attached to the circumference of the snare loop 204. In some instances, as shown, the actuation elements 206B, 206C may connect to the snare loop 204 at diametrically opposite locations. The proximal ends of actuation elements 206B, 206C may connect to an actuation element 206A within lumen 210A. Actuation element 206A extends proximally to connect to the actuation mechanism 214, as discussed in detail below. In some embodiments, the actuation elements 206B, 206C may connect individually to the actuation mechanism 214.

In certain embodiments, actuation element 206A may be relatively stiff and may embody a rod or hypo tube to improve the force transfer between the actuation mechanism 214 and snare loop 204.

Handle 208 may be ergonomic to allow the operator to easily hold and control the resection device 200, as well as operational elements that open and close snare loop 204. Handle 208 may embody any shapes are known in the art, and in some embodiments, the handle 208 may be of a generally cylindrical shape with rounded edges. Similarly, the dimensions of the handle 208 may be adapted to facilitate the operator to hold and control the resection device 200. Within the body of handle 208, the proximal end of actuation element 206A may attach to actuation mechanism 214, such as control member 216. The control member 216 may be a switch, knob, leaver, pulley, slider or the like, adapted to allow the physician to effectuate proximal and distal movement of actuation element 206A. In the illustrated embodiment, for example, control member 216 may be a slider configured to slide in a confined path within the handle 208.

A wide range of materials may be used to make the resection device 200 and its components. Suitable materials may include metals, polymers, metal-polymer composites, and the like. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene-terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These are just examples and must not be seen as limiting.

The catheter shaft 202 may be made of one or more suitable polymeric or metallic materials known in the art, for example the materials discussed above. In some implementations, a combination of materials may be employed. A suitable combination material may be a polymeric material reinforced with metallic wires, braid, or springs. Another suitable combination material may include short concentric polymeric and metallic tubes joined together in an alternating fashion to form the tubular portions (202A, 202B, and 202C). The polymeric tubes may provide flexibility, while the metallic tubes may provide rigidity to the tubular portions (202A, 202B, and 202C). Flexibility may allow the tubular portions (202A, 202B, and 202C) to traverse circuitous paths, while stiffness may allow an operator to urge the tubular portions (202A, 202B, and 202C) forward. Further, in some other embodiments, 3D printing techniques may be employed to make metallic or polymeric structures with desired thickness, stiffness, or other desired properties.

The snare loop 204 and the actuation elements 206A, 206B, and 206C may be made up of suitable polymeric or metallic materials known in the art, for example the materials discussed above. In general, the snare loop 204 and the actuation elements 206A, 206B, and 206C may be made up of electrically conducting, biocompatible material. The electrically conducting property of the material may facilitate cautery cutting, and biocompatibility of the material may prevent any inadvertent reaction between the snare loop 204 and the surrounding tissue. Further, the material of the snare loop 204 may have suitable stiffness to resect tissue and the material of the actuation elements 206A, 206B, and 206C may have suitable strength to transmit force from the actuation mechanism 214 to the snare loop 204.

The handle 208 may be made of suitable polymeric or metallic materials known in the art, for example the materials discussed above. In some embodiments, a combination of materials may be employed. For example, rigid structures within the handle 208 may be made of metallic materials to provide strength and stability to the handle 208, and the flexible structures within the handle 208 may be made of polymeric materials. For example, the handle 208 may have a metallic core to provide strength, and a polymeric covering to provide a better grip for the operator.

The resection device 200 or its components may include coatings. For example, suitable low-friction material, such as TEFLON®, polyetheretherketone (PEEK), polyimide, nylon, polyethylene, or other lubricious polymer coatings may be applied over the components of the resection device 200 to facilitate their operation. For example, lubricious coatings may be applied on the catheter shaft 202 to facilitate insertion through a body lumen or surgical insertion.

Further, to detect the position of catheter shaft 202 within a patient's body, at least some portions of the catheter shaft 202 may include radiopaque materials such as gold, palladium, platinum, tantalum, tungsten alloy, or polymeric materials loaded with radiopaque agents, such as barium sulfate ($BaSO_4$) or bismuth sub carbonate ($(BiO)_2CO_3$).

Radiopaque materials are capable of producing a relatively bright image on a fluoroscopic monitor or other imaging device, and may therefore facilitate identification of a position and/or orientation of catheter shaft 202.

Furthermore, the components of resection device 200 that come in contact with the patient's body may be coated with an anti-bacterial coating to inhibit bacterial growth on their surfaces. The anti-biotic coating may contain an inorganic anti-biotic agent, disposed in a polymeric matrix that may aid the antibiotic agent to adhere to the surface of the components of the resection device 200. Moreover, a drug-releasing coating may also be applied to the resection device 200 to assist in delivery of drugs to the severing site.

Figure 3A:
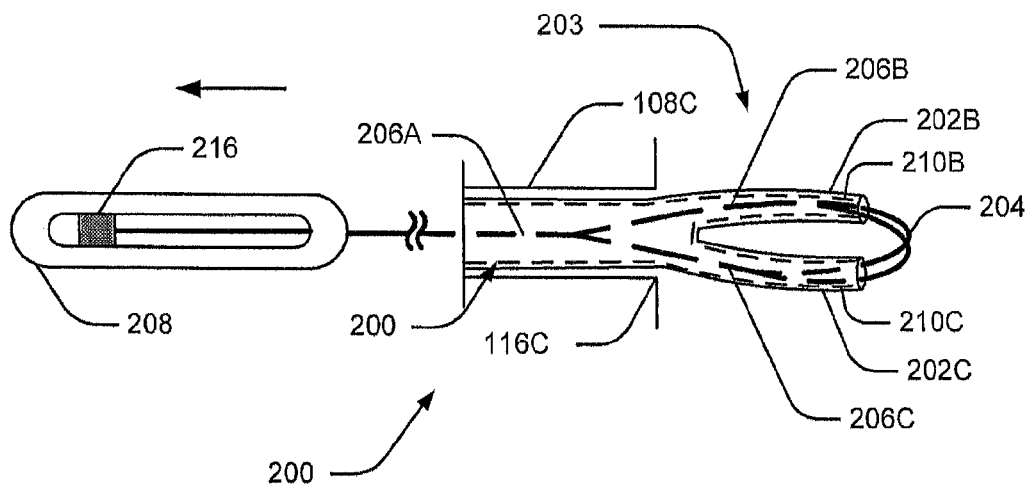
FIGS. 3A and 3B illustrate operation of the exemplary resection device of FIG. 2.
Figure 3B:
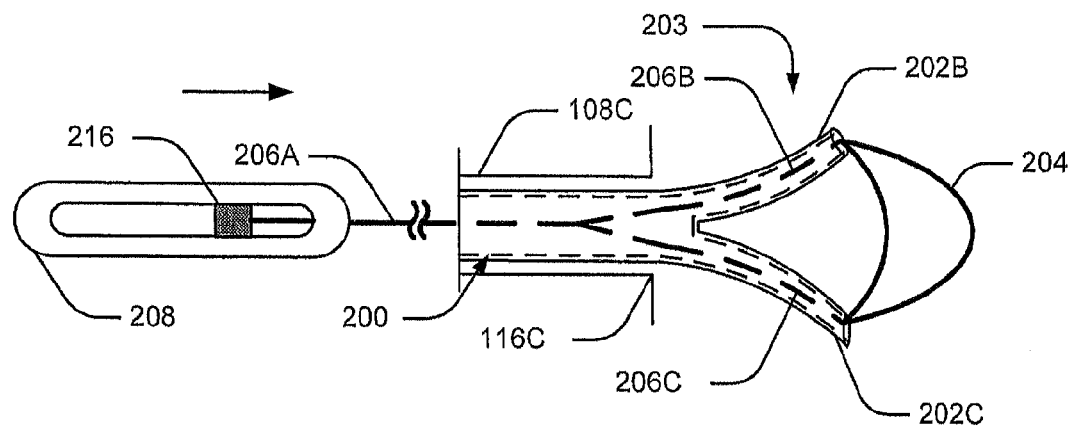

FIGS. 3A and 3B illustrate operation of the exemplary resection device 200.

Initially, as discussed above, resection device 200 is inserted into a channel 108C of an introduction sheath 102, which may be inserted into a patient's body and navigated to a treatment site. As shown in FIG. 3A, once the distal portion 106 of introduction sheath 102 is in position, catheter shaft 202 may be advanced until at least the distal branch portions 202B, 202C are extended out from opening 116C. When extended, distal branch portions 202B, 202C may be configured to assume an open configuration, expanding from the first position to the second position such that their distal ends substantially form a Y shape (e.g., as shown in FIG. 3B). In other words, the distal branch portions 202B, 202C, may extend from the introduction sheath 102, with snare loop 204. As a consequence of the distal branch portions 202B and 202C expanding, snare loop 204 may also deploy and open to its pre-formed shape. More particularly, as the distal branch portions 202B, 202C may extend from the introduction sheath 102 with snare loop 204, the snare loop 204 may open as the distal branch portions 202B, 202C may extend and open, as illustrated in FIG. 3B. Snare loop 204 may extend between the distal branch portions 202B, 202C.

In one implementation, snare loop 204 may be retracted to collapse the distal branch portions 202B, 202C. More particularly, an actuation element 206A may be retracted to close snare loop 204 and pull the proximal ends of the actuation elements 206B, 206C within the lumens 210B, 210C. Retraction of snare loop 204 may exert an inward-directed force on distal branch portions 202B, 202C, which may translate distal branch portions 202B, 202C from the open position to the closed position. Full movement of actuation element 206A may result in snare loop 204 being retracted into the lumens 210B and 210C, as well as returning distal branch portions 202B, 202C to their closed position.

FIG. 4 depicts an exemplary method of use of the resection device 200 to resect unwanted tissue. The operator may insert the introduction sheath 102 within a patient's body through a small incision in the stomach, femoral veins, or arteries, or through natural anatomical openings such as mouth, nose, anus, ureter, vaginal cavity, or the like. After introducing the introduction sheath 102, the operator may maneuver the introduction sheath 102 through the patient's body to reach a target location 400. In some embodiments, auxiliary devices carried in introduction sheath 102 can assist in the procedure. For example, illumination device 118 and/or optical device 120 may facilitate maneuvering the introduction sheath 102 as well as conducting the resection procedure. Once in position, the operator may distally extend the resection device 200 distally from the introduction sheath 102. That process may allow distal branch portions 202B, 202C to assume their pre-formed shapes and allow snare loop 204 to assume its open position.

With the snare loop 204 in position over a section of tissue 402 to be resected, the operator may proceed to apply power to the snare loop 204, if electrocautery is to be performed, and to resect the tissue 402 by retracting the snare loop 204 to its closed position. As the loop closes over the tissue 402, snare loop 204 may, by electrocautery and/or by cutting, resect the tissue 402. After resecting the desired tissue 402, the operator may then retract the resection device 200 within the introduction sheath 102, and retract the introduction sheath 102 from the patient's body. If retrieval of the resected tissue 402 is desired, snare loop 204 can be used as a retrieval device with the tissue sample disposed within the channel 108C. Alternatively, a number of other retrieval options are available, as known to those of skill in the art.

Referring to FIGS. 2-4, the use of the disclosed resection device 200 may provide significant advantages. For example, actuation of the snare loop 204 may be improved as compared to a traditional snare because the snare loop 204 is retracted from two attachment points, not just one as may be the case in conventional snares. As a result, the throw of control member 216 may be cut in half, which may improve operation and allow a physician to open and close a snare with substantially less longitudinal movement of a handle or actuation element. This may likewise permit the snare loop to be larger than conventional snares, while allowing a larger area of tissue to be resected with approximately the same throw of a control member.

The distal branch portions 202B and 202C may also provide support to the snare loop 204, which may prevent the snare loop 204 from deflecting when placed over the tissue 402, improving traction and reducing snare loop 204 slippage. In addition, the distal branch portions 202B and 202C may facilitate smooth closure of the snare loop 204 by reducing the maximum displacement and strain of ensnared tissue 402.

Embodiments of the present disclosure may be used in any medical or non-medical procedure, including any medical procedure where appropriate. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device, comprising:
an elongate member having a proximal end, a distal end, and a first lumen formed therein, wherein the distal end splits into a first distal branch portion having a second lumen, and a second distal branch portion having a third lumen, and the first distal branch portion and the second distal branch portion are each directly fixedly coupled to the distal end of the elongate member, wherein the first and second distal branch portions are movable between a first position, wherein the first and second distal branch portions are disposed relative to one another at a first angle, and a second position, wherein the first and second distal branch portions are positioned relative to one another at a second angle greater than the first angle;

a snare loop configured to transition between a collapsed configuration and an expanded configuration, and disposed at least partially within the first distal branch portion and the second distal branch portion when in the collapsed configuration; and first and second actuation elements extending, respectively, through the second and third lumens.

2. The medical device of claim 1, wherein the second and third lumens are in communication with the first lumen and branch from a same point at a distal end of the first lumen.

3. The medical device of claim 1, wherein portions of the snare loop are retracted within the second and third lumens when the first and second distal branch portions are in the first position.

4. The medical device of claim 1, wherein the first and the second actuation elements in the first and second distal branch portions are connected to a proximal actuation element in the first lumen.

5. The medical device of claim 1, wherein the first and the second actuation elements in the first and second distal branch portions are connected to separate actuation elements in the elongate member.

6. The medical device of claim 1, wherein the first and the second actuation elements affect movement of the first and second distal branch portions between the first and second positions.

7. The medical device of claim 1, further including a sheath disposed over the elongate member.

8. The medical device of claim 7, wherein the sheath is configured to extend over the first and second distal branch portions to affect movement of the first and second distal branch portions between the first and second positions.

9. The medical device of claim 1, wherein the first and the second actuation elements, and the snare loop, are configured to conduct electricity.

10. The medical device of claim 1, wherein the first actuation element is attached to the snare loop at a first joint, and the second actuation element is attached to the snare loop at a second joint.

11. The medical device of claim 10, wherein the first and second joints are located on opposite sides of the snare loop.

12. The medical device of claim 1, wherein the second lumen and the third lumen are each in communication with the first lumen of the elongate member.

13. The medical device of claim 1, wherein a proximal end of the first distal branch portion, and a proximal end of the second distal branch portion, are each directly fixedly coupled to the distal end of the elongate member.

14. A medical device, comprising:
an elongate member having a proximal end, a distal end, and a first lumen formed therein, wherein the distal end splits into a first distal branch portion having a second lumen, and a second distal branch portion having a third lumen;
a snare loop configured to transition between a collapsed configuration and an expanded configuration, and disposed at least partially within the first distal branch portion and the second distal branch portion when in the collapsed configuration;
a first actuation element slidably disposed within the first lumen of the elongate member;
a second actuation element slidably disposed within the second lumen; and
a third actuation element slidably disposed within the third lumen; wherein the second and third actuation elements are connected at respective proximal ends to the first actuation element and at respective distal ends to the snare loop.

15. The medical device of claim 14, wherein the first distal branch portion and the second distal branch portion are each directly fixedly coupled to the distal end of the elongate member.

16. A medical device, comprising:
an elongate member having a proximal end, a distal end, and a first lumen formed therein, wherein a distalmost end of the first lumen splits into a first distal branch portion having a second lumen, and a second distal branch portion having a third lumen, wherein the first and second distal branch portions are movable between a first position, wherein the first and second distal branch portions are disposed relative to one another at a first angle, and a second position, wherein the first and second distal branch portions are positioned relative to one another at a second angle greater than the first angle;
a snare loop configured to transition between a collapsed configuration and an expanded configuration, and disposed at least partially within the first distal branch portion and the second distal branch portion when in the collapsed configuration; and
first and second actuation elements extending, respectively, through the second and third lumens.

* * * * *